United States Patent [19]

Davis et al.

[11] Patent Number: 5,062,299

[45] Date of Patent: Nov. 5, 1991

[54] APPARATUS AND METHOD FOR DETECTING INHOMOGENEITIES IN SEMI-PLASTIC SUBSTANCES THROUGH ULTRASOUND

[75] Inventors: Ray E. Davis; Dana L. Duncan, both of Old Lyme; Samir W. Habboosh, Norwich; James R. Hall, Clinton; Dennis L. Nudelman, Waterford; Michael J. Westkamper, Salem, all of Conn.

[73] Assignee: Lever Brothers Company, Division of Conopco, Inc., New York, N.Y.

[21] Appl. No.: 461,200

[22] Filed: Jan. 5, 1990

[51] Int. Cl.$^5$ .............................................. G01N 29/00
[52] U.S. Cl. ........................................ 73/609; 73/597; 73/598
[58] Field of Search ............... 73/61 R, 597, 598, 600, 73/609, 627, 629

[56] References Cited

U.S. PATENT DOCUMENTS

| | | | |
|---|---|---|---|
| 3,237,623 | 3/1966 | Gordon | 73/629 |
| 3,832,887 | 9/1974 | Zeutschel | 73/598 |
| 3,961,307 | 6/1976 | Hochheimer et al. | 73/609 |
| 4,044,273 | 8/1977 | Kanda et al. | 310/335 |
| 4,208,915 | 6/1980 | Edwards | 73/620 |
| 4,384,476 | 5/1983 | Black et al. | 73/61 R |
| 4,509,360 | 4/1985 | Erwin et al. | 73/61 R |
| 4,574,624 | 3/1986 | Lehtinen et al. | 73/629 |
| 4,821,558 | 4/1989 | Pastrone et al. | 73/61 R |
| 4,821,573 | 4/1989 | Nagata et al. | 73/599 |
| 4,876,727 | 10/1989 | Maurer et al. | 73/598 |

Primary Examiner—Hezron E. Williams
Assistant Examiner—Craig Miller
Attorney, Agent, or Firm—Milton L. Honig

[57] ABSTRACT

A method and apparatus is reported for detecting inhomogeneities in semi-plastic substances such as toilet bars containing soap. An ultrasound probe is utilized to test the substance at an exit orifice of an extruder. Best results are obtained by utilizing a ceramic ultrasonic probe, rectangular in shape including a transducer having a concave curvature on a lower surface thereof. The probe includes a thermoplastic delay material. Ultrasonic waves directed through the probe preferably have a frequency between 1 and 2.25 MHz. Wedging of the extruded substance is also useful to improve contact with the probe as it passes through the extruder exit orifice.

32 Claims, 2 Drawing Sheets

APPARATUS AND METHOD FOR DETECTING INHOMOGENEITIES IN SEMI-PLASTIC SUBSTANCES THROUGH ULTRASOUND

BACKGROUND OF THE INVENTION

1. Field of the Invention

This invention relates to an apparatus and method for detecting inhomogeneities in semi-plastic substances, such as soap bars, through the use of ultrasound.

2. The Related Art

Ultrasound has been used in many fields as a non-destructive, non-invasive testing and diagnostic technique. It has been employed industrially for measuring the thickness of machined parts, monitoring corrosion inside pipes and vessels, finding flaws in welds and castings, and in measuring material properties. In medicine, it is used widely as a diagnostic imaging tool for scanning the abdomen, heart and other areas to detect disease or abnormalities.

A variety of consumer products have been monitored for quality control through ultrasound. For instance, U.S. Pat. No. 4,208,915 (Edwards discloses a method for determining by ultrasonic frequency detection foreign material in food products. A plurality of transducers are disposed in a rotatable cylinder having a liquid conductor. The cylinder having a surrounding flexible wall is compressed against the top surface of food products being transported beneath the cylinder on a conveyor belt. Food items stated to be suitable for examination are meat patties, fish fillets, boneless chicken products and, especially, hamburgers. Typical foreign objects include metal, bone particles, hair and pieces of cloth.

Fluid processed foodstuffs can also be inspected ultrasonically as reported in U.S. Pat. No. 4,384,476 (Black et al.). Among the foodstuffs amenable to inspection by this technique are flowable pasty or comminuted fruits and vegetables, ketchup, ground meats and soups. Also monitorable are aqueous slurries of fruits and vegetables which may be checked for unremoved pits, seeds, stems or even for rotten cores. The method involves transporting the foodstuff through a pipeline that includes an inspection station formed from a light transparent plastic. A curtain of ultrasonic sound is passed through an entire cross-section of the fluid foodstuff passing through the inspection station. Individual transducers are reported to be of a ceramic solid solution of lead zirconate and lead titanate dimensioned such that they oscillate and may be driven at a frequency of approximately 2.25 MHz.

U.S. Pat. No. 4,822,573 quality tests food filled packages subject to spoilage. The inspection method involves shaking each package in an agitation device and downstream therefrom passing the package between a package body thickness limiter immersed in a water tank wherethrough the ultrasound is transmitted. The useful wavelength region is stated to be between 0.5 and 20 MHz.

In the *Journal of the American Oil Chemists' Society*, 1984, 61(3) 560–564, there has been reported the use of ultrasound to investigate solid fat index dilatation during solidification of oils and fats. A doctoral dissertation has even been written about the technique as it relates to cheese wheys, margarines, and frozen dessert mixes. See *Dissertation Abstracts International*, B 1972, 33(4) 1604–1605.

Beyond foods, ultrasound has been employed to investigate solids levels in mouthwashes (J. Pharm. Sci., 67(4), 492–6 (1978)) as well as with cosmetic creams (Izv. Vyssh. Uchebn. Zaved., Pishch. Tekhnol., (5), 34–7 (1988)).

Most of the foregoing art has focused upon substrates that are either solids or substantially liquids. The probe of these type materials is a reasonably straight-forward task. Detectors can readily make contact and these materials echo easily interpretable signals. On the other hand, semi-plastic substances are not easily amenable to being probed. Difficulties in contact between probe and substance as well as interpretation of signals arise in this area.

Accordingly, it is an object of the present invention to provide an apparatus and method for detecting inhomogeneities within a semi-plastic substance.

A more specific object of the present invention is to provide an apparatus and method for detecting inhomogeneities such as foreign materials, undesirable phase structures, crystallinity and excess moisture in semi-plastic substances through the use of ultrasound.

A further object of the present invention is to provide an apparatus and method for detecting metal, glass, wood or other such foreign objects in toilet bars containing soap.

SUMMARY OF THE INVENTION

A method for detecting inhomogeneities in a semi-plastic substance is herewith provided, through steps comprising:

(a) extruding a flow of semi-plastic substance through an orifice;

(b) generating an ultrasonic wave and emitting the wave through an ultrasonic probe, the probe including an ultrasound delay material at one end thereof, the delay material being in solid form, and the probe being positioned at the orifice;

(c) contacting the delay material against a face of the substance as the substance exits the orifice;

(d) directing the wave from the probe through the delay material and then through the flow;

(e) receiving a signal based on a return of the wave passing through the flow; and (f) analyzing the signal by means of a program comparing the signal to a reference value.

The above described method is particularly suited to the detection of foreign material such as pieces of metal, glass, paper, wood and the like in a toilet bar containing soap. Other inhomogeneities may also be monitored including proper phase structure, moisture content and crystallinity.

Additionally there is disclosed an apparatus for detecting inhomogeneities in a semi-plastic substance, the apparatus comprising:

(a) an extruder for mixing the semi-plastic substance, the extruder at a downstream end thereof including an exit orifice;

(b) an ultrasonic probe positioned at the exit orifice; the probe including an ultrasound delay material in solid form positioned to contact the semi-plastic substance as the substance passes through the exit orifice; and (c) a means for analyzing a return signal that was directed by the probe and has passed through the semi-plastic substance, the analysis including comparison of the return signal to a reference value.

BRIEF DESCRIPTION OF THE DRAWINGS

The above objects, features and advantages of the invention will become more readily apparent from consideration of the drawing wherein.

DETAILED DESCRIPTION OF THE INVENTION

Figure 1:
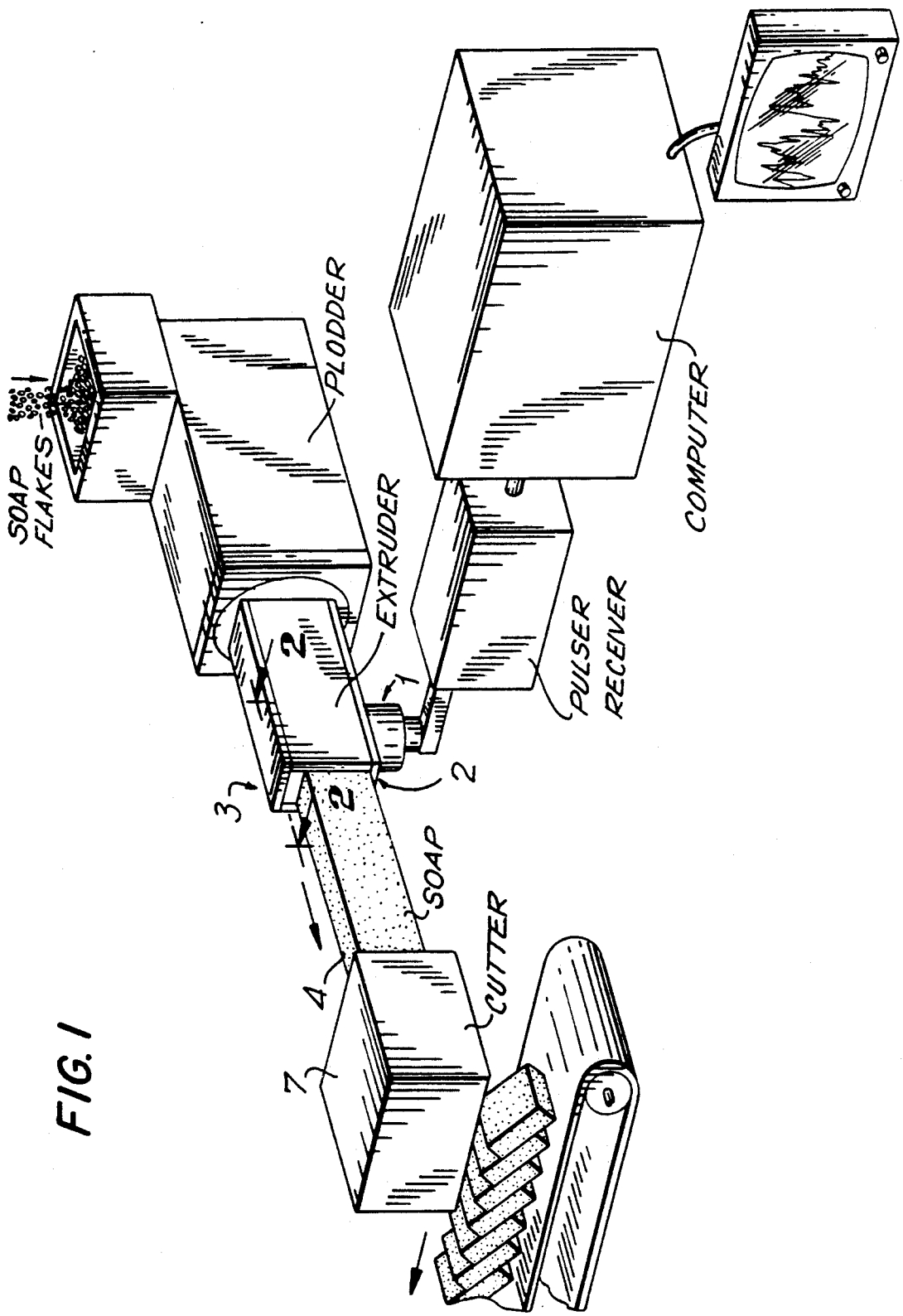
FIG. 1 schematically illustrates the overall apparatus including extruder, ultrasonic probe and cutter.

Now it has been found that semi-plastic substances can be monitored for quality control or process regulation through ultrasound analysis by positioning an ultrasonic probe 1 at an exit 2 of an extruder 3. As semi-plastic product 4 emerges at the exit 2 of the extruder, the probe through an end fitted with a solid delay material 5 contacts an outer surface 6 of the extruded substance. FIG. 1 illustrates the overall apparatus. Of particular advantage in sensing at the extruder exit 2 is that this avoids sensing of a full vat of substance in gross which would contain both satisfactory and unsatisfactory fractions. On the other hand, the chosen point of sensing avoids evaluating each substance separately when it has been formed into a small article, e.g. separate toilet bars. Thus, the invention has focused on the most advantageous point in the process for probing, a point subsequent to formulation of the semi-plastic but prior to its breakup, e.g. through a cutter 7, into individual semi-plastic articles.

Transducer Selection—General Principles

Before further details of this invention are delineated, a general overview of ultrasound principles would assist in understanding the invention. A key element of the ultrasound probe is a transducer. A pulser unit supplies necessary high voltage electrical energy to excite a surface of the transducer. Mechanical oscillations resulting therefrom are transmitted into the test material, i.e. the semi-plastic substance, via a suitable coupling agent. Returning sound waves are then processed by a receiver. These waves may be displayed on an oscilloscope in the form of amplitude versus time (A-Scan). This pulse-echo technique is capable of detecting impurities which cause a sufficient "discontinuity" in the test material structure.

Discontinuities occur at interfaces where there is a sudden change in the acoustic properties of the test material. If a plain sound wave front strikes an interface between two different media, a portion of the wave is reflected with remaining energy passing through the interface. The ratio of the sound pressure of the reflective wave versus the transmitted wave depends primarily on the acoustic impedance, Z (Z =density of material x speed of sound in material), of the adjoining materials, and the surface structure and size of the reflector. Particles with a characteristic speed of sound or density much different from that of the test material, e.g. soap versus steel, will produce strong echo returns and thus will be easier to detect.

The relative effectiveness of transducers in detecting impurities depends on many factors. These include the geometry of the transducer, operating frequency, material construction, pulser, and receiver. The sound pressure distribution in space of ultrasonic units is a direct consequence of its material composition and geometry of the probe under consideration. Theoretical analysis indicates variously shaped probes share common characteristics in their energy distribution. High frequency sound waves exhibit high directionality with the most significant portion of the sound field concentrated in a sector known as the sound beam. In a region immediately in front of the transducer crystal there is an area with strong sound pressure variations, including null energy spots, referred to as the near zone (Fresnel zone). Attempts to detect inclusions within the near zone can lead to unreliable results and thus the working range of the probe should be designed to eliminate or avoid this zone. An estimate for the near field of circular transducers can be determined from the following equation:

$$\text{Near field} = Nf$$

$$Nf = \frac{d^2}{4 * \text{lambda}} = \frac{d^2 * f}{4 * c} \quad [1]$$

where:
d = transducer diameter
lambda = wave length
f = frequency
c = local speed of sound Smaller diameter crystals, lower operating frequencies and materials with a fast local speed of sound will produce shorter near field lengths. The near field inhomogeneity of a rectangular transducer is less marked than that of a circular transducer of similar size. As a rough guide, the near field of a rectangular transducer extends for a distance somewhat beyond that of a circular transducer of diameter equal to the maximum length of the rectangle. Constructive interference of plane sound waves creates regions of high pressure within the near field. The point of the last axial maximum defines the transition between the near zone and far zone (Fraunhofer zone). The near field decreases from an approximate diameter of that of the crystal to about half that size at the end of the near field. At this point the sound beam is concentrated to its greatest extent.

In the far field the sound beam begins to diverge with an approximate half angle, gama of:

$$gama = divergence\ angle$$

for disc oscillators:

$$gama\ (6\ dB\ down) = arc\ \sin\ (0.51 * lambda)/d$$

$$gama\ (20\ dB\ down) = arc\ \sin\ (0.87 * lambda)/d$$

for rectangular oscillators:

$$gama\ (6\ dB\ down) = arc\ \sin\ (0.44 * lambda)/s$$

$$gama\ (20\ dB\ down) = arc\ \sin\ (0.74 * lambda)/s$$

where:
lambda = wave length
d = diameter of crystal
s = side of the rectangular oscillator In general for unfocused transducers, larger diameter crystals with high operating frequencies produce more coherent sound beams. For all crystals, regardless of shape, the far field pressure amplitude decreases with distance due to the divergence of the beam. In addition, the material structure absorbs some of the acoustic energy, converting sound into heat. This combined with losses induced from scattering at microscopic interfaces is referred to as sound attenuation. Energy decays in an exponential manner in relation to distance:

$$\frac{p(z)}{po} = e^{(-2 \cdot alpha \cdot z)}$$

where:
p(z)=pressure at distance z from transducer face
po=originating pressure
alpha=attenuation coefficient (for a given material this value varies depending on frequency of oscillator)
z=distance from transducer surface Total decrease in sound energy is an accumulation of distance losses and attenuation.

Delay Material

We have determined from our studies that, in general, probes with higher echo returns suffer from a resolution problem with semi-plastic substances in the frontal portion of the signal. This affect leads to unacceptable near surface detection of particles. Attempts to decrease these initial main bang oscillations with a built-in receiver damping circuit was found to produce a large decrease in overall signal strength, indicating that transducers with high damping would result in probes with poor particle detection properties.

Figure 3:
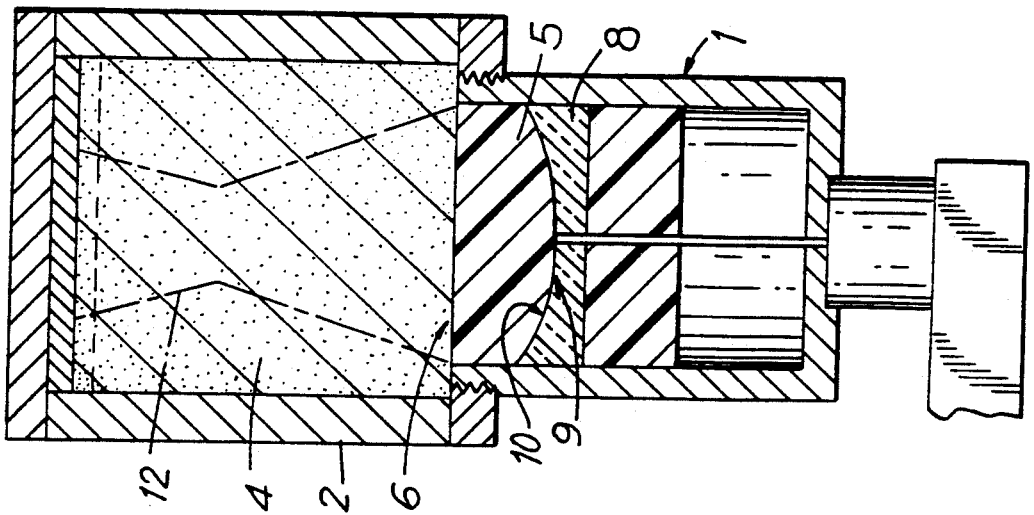
FIG. 3 is a cross section of the extruder-probe area taken along line 3—3 of FIG. 2.
Figure 2:
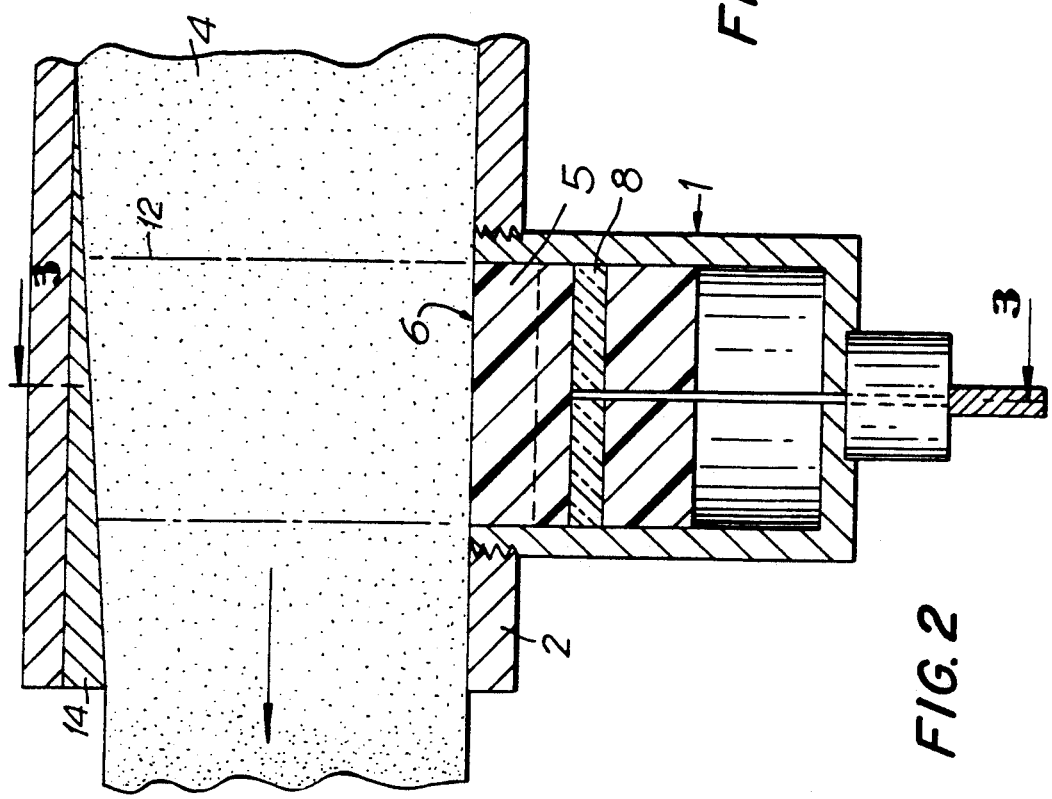
FIG. 2 is a cross section of the extruder-probe area taken along line 2—2 of FIG. 1.

According to the invention, the problem has now been solved by employing a delay material 5 of specific construction for interfacing between the substance 4 to be tested and the transducer 8 of the probe 1. This delay material 5 provides sufficient damping to reduce frontal oscillations but insufficient to attenuate the entire signal. A cleaner and dramatic increase in surface particle detection has been achieved. FIG. 2 and 3 schematically illustrate the probe with its components.

Selection of the delay material 5 depends on several factors. Material composition must withstand high temperatures (above about 140° F.), humidity and caustic chemicals involved in extruding semi-plastics such as soap. A material with a high local speed of sound was found necessary to reduce the near field length. Also necessary was for the material to have an acoustic impedance close to that of the semi-plastic substance to allow for more efficient transmission of sound energy into that substance.

Based upon the aforementioned considerations, the best delay material was in the form of a solid with an impedance ranging from 0.20 to 1.0, preferably from about 0.25 to about 0.50, optimally between about 0.28 and about 0.45 (gm/cm$^2$-sec)$\times 10^6$.

Under conditions where the extruder exit is heated, it is important that the delay material have a melting point greater than 110° F. and that it have good abrasion resistance.

Several plastic materials were found to meet the criterion necessary for an effective delay. Particularly preferred are thermoplastic polymers, examples of which include polyamides (nylon), polyethylene terephthalate, polycarbonate (Lexan, ex General Electric), polyacetal (Delrin, ex Dupont), polyphenylene oxide, polysulfone and formaldehyde melamine resins (Bakelite).

Transducer Construction

The transducer 8 is preferably formed from a ceramic. This material allows the transducer to withstand elevated temperatures and also to resist abrasion.

Geometry of both the transducer and delay material is important. Advantageously, an end 9 of the transducer in contact with the delay material 5 should have an outwardly concave curvature. Extent of curvature for the transducer end surface should be in an amount sufficient to focus a beam 12 near the center of the semi-plastic object being measured. The delay material should exhibit a complementary convex bulge 10 to directly contact the curved transducer.

Any geometry may usefully be employed as a lower surface of the delay material which contacts the substance to be tested. For these purposes, a round flat lower contact surface 11 has been found to be quite suitable.

A still further advantageous structural aspect is that the transducer 8 should be in the form of a rectangular elongate bar. The rectangular elongate geometry was found necessary to provide adequate ultrasound contact with the extruded substance that continuously moves outward from the extruder exit. Ratio of length to width of the transducer should range from about 5:1 to about 1.2:1, preferably between about 2:1 to 1.75.

All of the foregoing transducer structural features have been formulated to achieve the optimum in a focused sharp knife-edge line of energy. This focused beam provides a very good return signal to monitor in contrast to signals generated from a dispersed entry beam having weak force.

Mounting System

The mounting system for the transducer should be so designed that it can be bolted directly to the extruder head. This system must be capable of keeping the transducer in direct contact with the semi-plastic surface insuring good signal return. With respect to soap substances it has been found that a contact pressure of from about 10 to 50 pounds per square inch, optimally about 30 pounds per square inch, is sufficient to insure the required signal levels.

An advantageous feature which allows the desired contact pressure is the employment of a wedge 14 in the exit orifice channel. Advantageously, the wedge may be integral with a wall of the exit orifice channel opposite to that of the delay material. The wedge should be so angled that it causes the extruded substance to be compressed as it passes downstream past the delay material lower surface. Wedging angle should be about 1 20 to about 10°, preferably between about 1° and 4°. This wedging action ensures tight contact between the substance and the delay material. Tight contact ensures sharper imaging of the ultrasonic wave.

Pulser Specification

Resonating frequencies of the transducer may also be important in achieving optimum results. Frequencies between about 1 and 4 MHz, preferably between 1.0 and 2.25 MHz, provide satisfactory results.

Operation of the transducer will normally require the input of anywhere from 100 to 1,000 volt, preferably 200–500 volt, impulse to resonate the test substance.

Optimum performance of the pulser unit will be at a 300 volt signal delivery for a duration of least ½ a wavelength. A suitable pulser is available from Harisonic Laboratories, Division of Stavely Sensors, Model MP127, and receiver unit Model MR106 which combination provides extremely good results because of the high power output and adjustment flexibility.

Semi-Plastic Substance

By semi-plastic substance is meant a substance liquifiable below 150° C. Consumer toilet bars are the most conspicuous commercial example of a semi-plastic material within the context of this invention. Most toilet bars contain a semi-solid surfactant, most often that of soap. Other surfactants may also be employed exclusively or in combination with soap. These substances include fatty acyl isethionate, fatty alkyl glycerol ether sulfonate, fatty alcohol sulfate, alpha-olefin sulfonate, acyl taurate, mono- and di-alkyl phosphate, dialkylamine oxide, alkyl sulfosuccinate, fatty acid or amido betaine, sulfobetaine, alkane sulfonate and mixtures thereof. Most preferably, soap will be present and in an amount of at least 5% by weight.

Inhomogeneities

Several types of flaws or foreign objects may be detected in the substance by the method of this invention. For not always well explained reasons, manufacture of semi-plastic substances such as toilet bars occasionally inadvertently includes undesirable foreign objects like small pieces of glass, wood chips, cardboard or metal. Bars with these contaminants must be apprehended before shipment to the consumer.

The apparatus and method of this invention may also be applied to the measurement of moisture content or phase structure in toilet bars. Phases may be that of the delta, kappa, gamma or zeta phases each of which is desirably controlled to obtain the desired performance properties. Crystallization within the substance may also lead to the undesired formation of sandy particles (known as "sand") for which ultrasound may serve as a useful probe. Transparency of milled soap may also be monitored by this method, phase structure and crystallization being significant factors in effecting transparency.

The following examples will more fully illustrate the embodiments of this invention. All parts, percentages and proportions referred to herein and in the appended claims are by weight of the total composition unless otherwise stated.

EXAMPLE 1

A toilet bar composition was prepared having the formulation appearing in Table I.

TABLE I

| Toilet Bar Formulation Containing Soap/Acyl Isethionate | |
|---|---|
| Components | Weight % |
| Sodium Soap (82/18)* | 50.73 |
| Sodium Cocoyl Isethionate | 21.74 |
| Water (final content) | 11.70 |
| Stearic Acid | 6.98 |
| Sodium Isethionate | 5.00 |
| Miscellaneous (perfume, colorants, preservatives) | 2.10 |
| Coconut Fatty Acid | 1.32 |
| Sodium Chloride | 0.43 |

*Tallow to coconut oil ratio

The components of Table I were blended together at a temperature of 230° F. with water being permitted to evaporate from the reactor. At the end of the reaction, the batch was discharged onto a chill roll at 100° F. The chill rolled chips were then milled. Milled material was then refined and then extruded into logs through an 6 inch refiner/plodder. Temperatures varied between 95° and 110° F. in the plodder with plodding times of from 12 to 20 minutes.

At the exit of the plodder was placed an ultrasound probe whose transducer had dimensions of 0.75 inches width × 1.375 inches length formed of ceramic material with curvature as illustrated in FIG. 3. Operating frequency was at 1.0 megahertz. The extruder exit wall opposite the thermoplastic delay material was angled to achieve a decreasing soap wedge of 1°-4° angle.

Excellent detection was achieved for glass, wood chips and metal particles which were spiked to the batch prior to extrusion.

Subsequent to the ultrasound detection, the continuous log exiting the extruder was cut into toilet bar billets and removed by conveyor belt. Thereafter the billets were stamped with a logo.

EXAMPLE 2

In the context of the previous Example, herein is reported the effect of various resonating frequencies on the quality of the analysis. Table II provides this comparison.

TABLE II

| Resonating Frequency (MHz) | Signal Quality |
|---|---|
| 5 | No energy return observed |
| 1.0–2.5 | Satisfactory signal |
| 0.5 | No resolution to observe 1/32–1/16 inch impurity particles |

EXAMPLE 3

This Example illustrates the effect of variously shaped transducers on the signal quality. Table III outlines the results.

TABLE III

| Geometry | Signal Quality |
|---|---|
| Round transducer | Poor signal return |
| Rectangular transducer | Satisfactory signal quality |

The foregoing description and Examples illustrate selected embodiments of the present invention. In light thereof, various modifications will be suggested to one skilled in the art, all of which are within the spirit and purview of this invention.

What is claimed is:

1. A method for detecting inhomogeneities in a semi-plastic substance through steps comprising:
   (a) extruding a flow of said substance through and orifice;
   (b) generating an ultrasonic wave and emitting said wave outwardly through an ultrasonic probe, said probe including an ultrasound delay material at one end thereof, said delay material being a thermoplastic in solid form, and said probe being positioned at said orifice;
   (c) contacting said delay material against a face of said substance as said substance exits said orifice, said substance as it flows downstream past said delay material being wedged inwardly at an angle to achieve good contact between said substance and said material;
   (d) directing said wave from said probe through said delay material and then through said flow;
   (e) receiving a signal based on a return of said wave passing through said flow; and
   (f) analyzing said signal by means of a program comparing said signal to a reference value.

2. A method according to claim 1 wherein said semi-plastic substance is a toilet bar.

3. A method according to claim 2 wherein said toilet bar is formed at least in part from a surfactant.

4. A method according to claim 3 wherein said surfactant is soap.

5. A method according to claim 4 wherein the soap is present in an amount of at least 5%.

6. A method according to claim 3 wherein the surfactant is selected from the group consisting of soap, fatty acyl isethionate, fatty alkyl glycerol ether sulfonate, fatty alcohol sulfate, alpha-olefin sulfonate, acyl taurate, mono- and di-alkyl phosphate, dialkylamine oxide, alkyl sulfosuccinate, fatty acid or amido betaine, sulfobetaine, alkane sulfonate and mixtures thereof.

7. A method according to claim 1 wherein said ultrasonic probe is formed from a ceramic.

8. A method according to claim 1 wherein said delay material is formed from a thermoplastic.

9. A method according to claim 8 wherein said thermoplastic is selected from the group consisting of polyamides, polyethylene terephthalate, polycarbonate, polyphenylene oxide, polysulfone, formaldehyde melamine resins and mixtures thereof.

10. A method according to claim 1 wherein said ultrasonic wave has a radio frequency ranging from about 1 to about 5 MHz.

11. A method according to claim 10 wherein said ultrasonic wave has a radio frequency ranging from 1.0 to 2.25 MHz.

12. A method according to claim 1 wherein said probe includes a transducer, a lower surface of said transducer having a concave structure.

13. A method according to claim 1 wherein said probe has rectangular measurements of length and width.

14. A method according to claim 1 wherein said angle of wedging is between 1° and 10°.

15. A method according to claim 1 wherein said inhomogeneities result from flaws selected from the groups consisting of foreign objects, moisture content, varying crystallinity and phase structure.

16. A method according to claim 15 wherein said foreign objects are selected from the group consisting of glass, wood chips, cardboard, metal pieces and mixtures thereof.

17. An apparatus for detecting inhomogeneities in a semi-plastic substance, the apparatus comprising:
(a) an extruder for mixing said semi-plastic substance, said extruder at a downstream end thereof including an exit orifice;
(b) an ultrasonic probe positioned at said exit orifice, said probe including an ultrasound delay material in solid form positioned to contact said semi-plastic substance as said substance passes through said exit orifice, said exit orifice including therewith a channel formed with a decreasing diameter thereby causing said semi-plastic substance to wedge inwardly at an angle to achieve good contact between said substance and said delay material; and
(c) a means for analyzing a return signal that was directed by said probe and has passed through said semi-plastic substance, said analysis including comparison of said return signal to a reference value.

18. An apparatus according to claim 17 wherein said ultrasonic probe is formed from a ceramic.

19. An apparatus according to claim 17 wherein said delay material is formed from a thermoplastic.

20. An apparatus according to claim 19 wherein said thermoplastic is selected from the group consisting of polyamides, polyethylene terephthalate, polycarbonate, polyphenylene oxide, polysulfone, formaldehyde melamine resins and mixtures thereof.

21. An apparatus according to claim 17 wherein said ultrasonic waves have a radio frequency ranging from about 1 to about 5 MHz.

22. A apparatus according to claim 21 wherein said ultrasonic wave has a radio frequency ranging from 1.0 to 2.25 MHz.

23. An apparatus according to claim 17 wherein said probe includes a transducer, a lower surface of said transducer having a concave structure.

24. An apparatus according to claim 17 wherein said probe has rectangular measurements of length and width.

25. An apparatus according to claim 17 wherein said channel is formed to achieve an angle of wedging between 1° and 10°.

26. An apparatus according to claim 17 wherein a soap plodder is attached to said extruder at an upstream end thereof.

27. A method for detecting inhomogeneities in a semi-plastic substance which is formed at least in part from a surfactant, said method including steps comprising:
(a) extruding a flow of said substance through an orifice;
(b) generating an ultrasonic wave and emitting said wave outwardly through and ultrasonic probe, said probe having rectangular measurements of length and width and including an ultrasound delay material at one end thereof, said delay material being a thermoplastic in solid form, and said probe being positioned at said orifice;
(c) contacting said delay material against a face of said substance as said substance exits said orifice;
(d) directing said wave from said probe through said delay material and then through said flow;
(e) receiving a signal based on a return of said wave passing through said flow; and
(f) analyzing said signal by means of a program comparing said signal to a reference value.

28. A method according to claim 27 wherein said surfactant is soap.

29. A method according to claim 27 wherein said thermoplastic is selected from the group consisting of polyamides, polyethylene terephthalate, polycarbonate, polyphenylene oxide, polysulfone, formaldehyde melamine resins and mixtures thereof.

30. An apparatus for detecting inhomogeneities in a semi-plastic substance, the apparatus comprising:
(a) an extruder for mixing said semi-plastic substance, said extruder at a downstream end thereof including an exit orifice;
(b) an ultrasonic probe positioned at said exit orifice, said probe including an ultrasound delay material having rectangular measurements of length and width and being a thermoplastic which is in solid form positioned to contact said semi-plastic substance which is formed at least in part from a surfactant, as said substance passes through said exit orifice; and
(c) a means for analyzing a return signal that was directed by said probe and has passed through said semi-plastic substance, said analysis including comparison of said return signal to a reference value.

31. An apparatus according to claim 30 wherein said surfactant is soap.

32. An apparatus according to claim 30 wherein said thermoplastic is selected from the group consisting of polyamides, polyethylene terephthalate, polycarbonate, polyphenylene oxide, polysulfone, formaldehyde melamine resins and mixtures thereof.

* * * * *